United States Patent [19]
Peters

[11] Patent Number: 5,407,430
[45] Date of Patent: Apr. 18, 1995

[54] INTRAVENOUS CATHETER

[76] Inventor: Michael J. Peters, 2196 Wycliffe, West Bloomfield, Mich. 48323

[21] Appl. No.: 215,304

[22] Filed: Mar. 21, 1994

[51] Int. Cl.$^6$ .................................... A61M 29/00
[52] U.S. Cl. .................................... 604/104
[58] Field of Search ............... 604/281, 282, 104, 105, 604/106, 107, 108, 264; 606/194

[56] References Cited

U.S. PATENT DOCUMENTS

| | | | |
|---|---|---|---|
| 3,996,938 | 12/1976 | Clark, III | 128/348 |
| 4,411,655 | 10/1983 | Schrick | 604/104 |
| 4,650,466 | 3/1987 | Luther | 604/95 |
| 4,655,771 | 4/1987 | Wallsten | 604/201 |
| 4,848,342 | 7/1989 | Kaltenbach | 606/194 |
| 4,954,126 | 9/1990 | Wallsten | 600/36 |
| 5,002,560 | 3/1991 | Marchold et al. | 604/104 |
| 5,122,122 | 6/1992 | Allgood | 604/105 |
| 5,158,545 | 10/1992 | Trudell et al. | 604/53 |
| 5,273,529 | 12/1993 | Idowu | 604/108 |
| 5,306,250 | 4/1994 | March et al. | 604/104 |

FOREIGN PATENT DOCUMENTS
9111209   8/1991   WIPO .................. 604/104

*Primary Examiner*—John D. Yasko
*Assistant Examiner*—Manuel Mendez
*Attorney, Agent, or Firm*—Lyman R. Lyon

[57] ABSTRACT

An expandable intravenous catheter for the infusion of fluids into a blood vessel comprises a helically wound tube having a diameter that can be varied from a normal minimum diameter to a relatively larger diameter by axial movement of the ends of the tube relative to each other, after insertion of the catheter into the blood vessel.

1 Claim, 2 Drawing Sheets

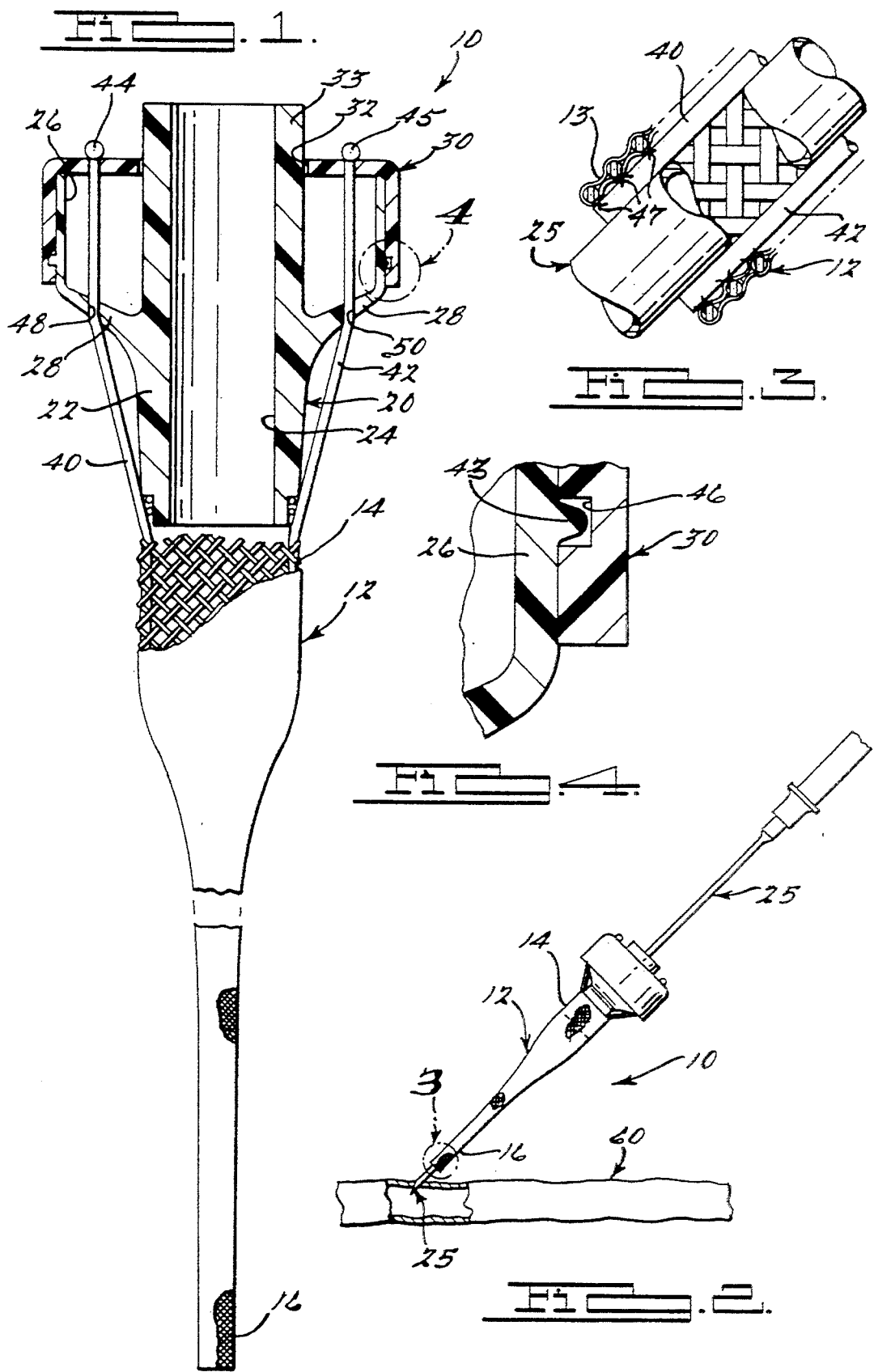

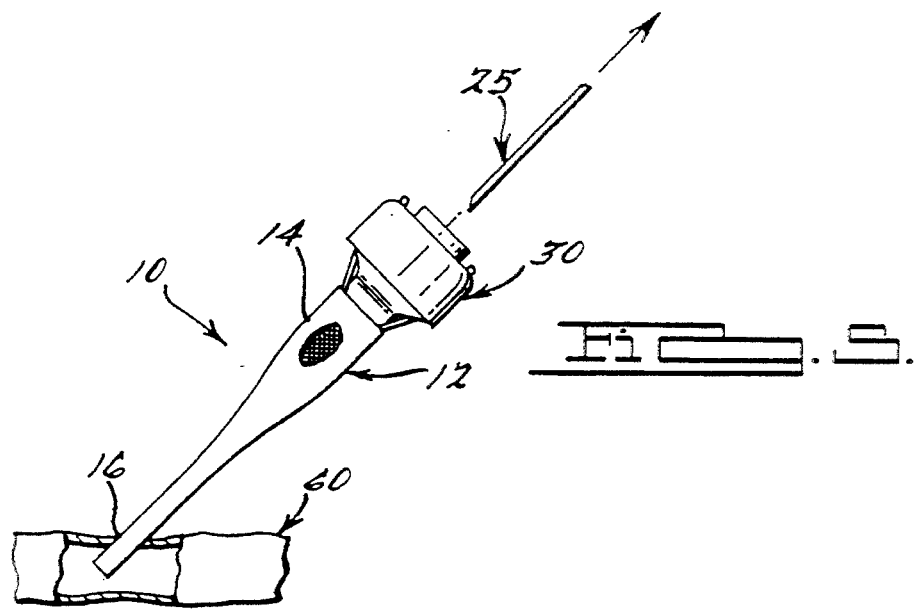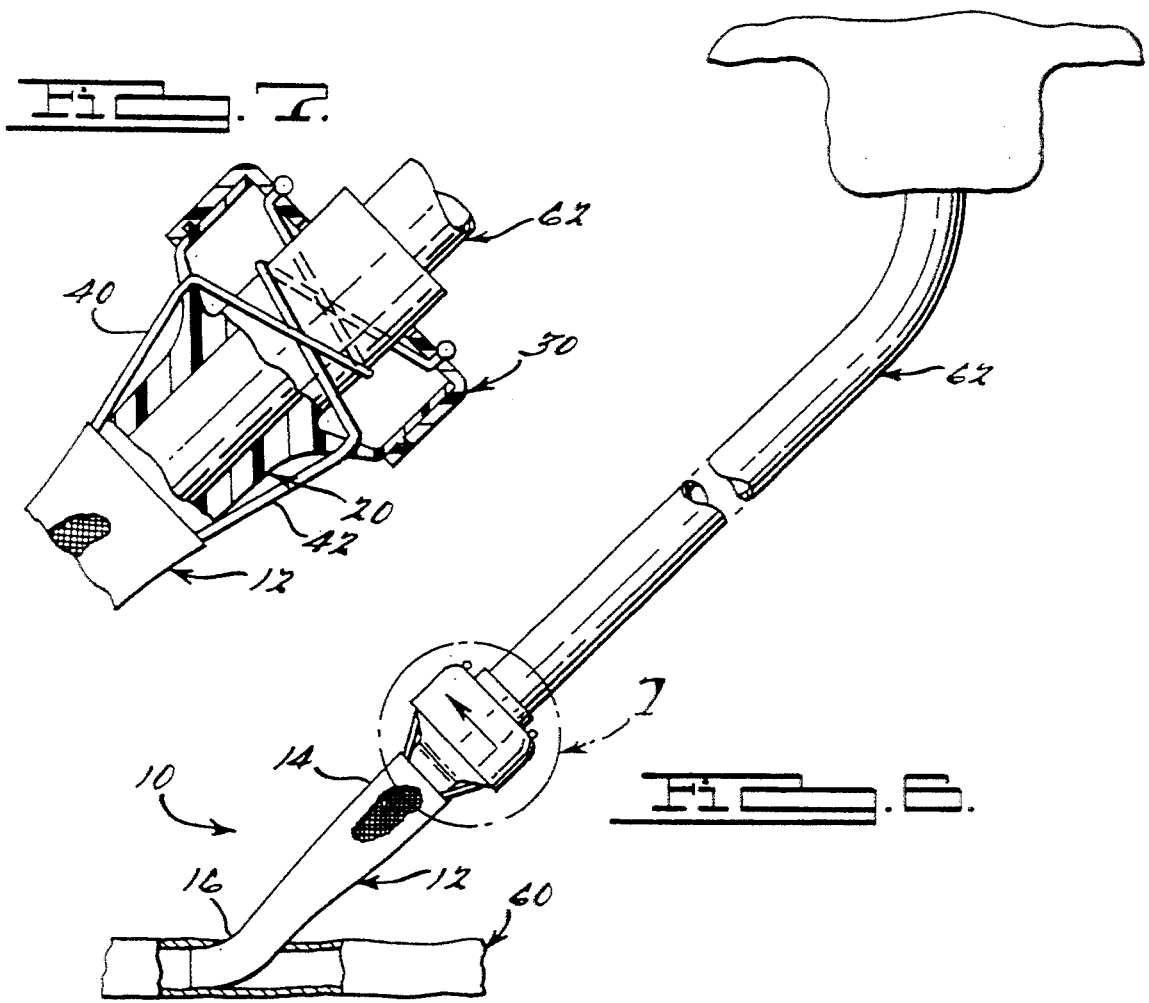

INTRAVENOUS CATHETER

This invention relates generally to intravenous catheters and more specifically to a controllable, variable diameter intravenous catheter.

BACKGROUND OF THE INVENTION

Intravenous catheters are generally utilized to slowly introduce fluids into the body. Occasionally, however, such catheters are required to rapidly introduce a large amount of fluid into the body. If, for example, a patient is hypovolemic and in shock or at risk of shock, the catheter is inserted into a patient's blood vessel and a large volume of fluid is rapidly delivered through the catheter.

In order to facilitate rapid, high-volume infusion of fluid into a blood vessel, the catheter should have an outside diameter equal to the maximum inside diameter of the blood vessel. However, such a catheter is obviously difficult to insert into the blood vessel. Furthermore, since a hypovolemic patient's blood vessels are often collapsed, it is often necessary to expand the blood vessel prior to the infusion of fluids.

Intravenous catheters are known which utilize a helically braided tube that inherently expands within the blood vessel after insertion. The tube is designed so that, in its natural state, its diameter is maximized by plastic memory order to use such known catheters, a sheath is telescoped thereover to condition the tube for insertion into a blood vessel. The radially constrained tube and its restraining sheath are inserted into the blood vessel. The sheath is then drawn from the blood vessel allowing the tube to expand to its natural state thereby expanding the blood vessel by exerting a radially outward bias on the walls thereof.

One problem with such known catheters is that the diameter thereof cannot be reduced after removal of the sheath. Thus, the catheter must be removed from the blood vessel while in the expanded state in which it exerts a bias upon the walls of the blood vessel. Removal of such known catheters has been known to abraid the walls of the blood vessel, encouraging subsequent blood clot formation.

SUMMARY OF THE INVENTION

The aforesaid problems are solved, in accordance with a preferred constructed embodiment of the present invention, by an intravenous catheter that, in the normal condition, is radially contracted by plastic memory to facilitate insertion thereof into a blood vessel. After introduction into the blood vessel, the catheter is mechanically radially expanded to facilitate the introduction of fluids. Release of the mechanically induced expansion permits the catheter to radially contract due to plastic memory to facilitate withdrawal thereof from the blood vessel.

More specifically, a fluid impervious tube has a braided helix supportive reinforcement manufactured so that in its natural state it is of minimum diameter. Radial expansion of the catheter is accomplished by mechanically shortening the helical reinforcement after insertion of the tube into the blood vessel. Mechanical shortening of the tube is accomplished by tensioning a pair of retraction cords which are attached to the insertion end of the catheter and to a rotatable catheter expansion control knob at an opposite end thereof. The rotatable control knob is journaled on a hub on the outer end of the catheter and has a straight, wide central passageway for the acceptance of a needle or a fluid supply tube.

The catheter is expanded by rotating the control knob on its supporting hub. When the knob is rotated, the retraction cords are wound about the hub so as to draw the insertion end of the catheter toward the rotatable element, concomitantly mechanically expanding the diameter thereof. When the control knob is subsequently rotated in the reverse direction, tension on the retraction cords is relieved and the catheter inherently returns to its natural, relative small diameter state due to plastic memory of the helical reinforcement.

The diameter of the catheter can be infinitely adjusted between a natural condition of minimum diameter and an expanded condition of maximum diameter by rotation of the control knob.

BRIEF DESCRIPTION OF THE DRAWINGS

FIG. 1 is an elevational view, partially in cross section, of a preferred embodiment of the catheter of the present invention;

FIG. 2 is a view of the catheter of FIG. 1 telescoped over a needle that has penetrated a blood vessel;

FIG. 3 is a view taken within the circle 3 of FIG. 2;

FIG. 4 is a view taken within the circle 4 of FIG. 1;

FIG. 5 is a view of the catheter after insertion into a blood vessel;

FIG. 6 is a view of the catheter after radial expansion within the blood vessel and insertion of a standard IV tube for delivery of fluid; and FIG. 7 is a sectional view taken within the circle of FIG. 6.

DETAILED DESCRIPTION OF THE PREFERRED EMBODIMENT

An intravenous catheter 10, in accordance with a preferred constructed embodiment of the present invention comprises a helically braided tube 12, wound so as to exhibit a minimum natural or inherent diameter. The tube 12 is covered by a fluid impervious flexible coating 13, for example a latex film, for the containment of fluids. When the ends 14 and 16 of the tube 12 are drawn toward each other, the tube 12 expands. Conversely, when the ends 14 and 16 of the tube 12 are free to move apart, the tube 12 narrows due to the inherent memory of the fibers thereof.

In accordance with the present invention, a hub 20 supports the outer end 14 of the tube 12. The hub 20 comprises an inner cylinder 22 that defines a passageway 24 through the center thereof, for the acceptance of, for example, a needle 25. The hub 20 has an outer cylinder 26 that surrounds the inner cylinder 22 in radially spaced coaxial relation and is connected thereto by a radial flange 28.

A rotatable element or control knob 30 is journaled on the outer cylinder 26 of the hub 20. The knob 30 has a central aperture 32 for the acceptance of an upper end portion 33 the inner cylinder 22 of the hub 20 which in turn provides access for the intravenous feed tube or needle 25.

A pair of retraction cords 40 and 42 are connected to the rotatable control knob 30 as by stops 44 and 45, respectively, and to the insertion end 16 of the tube 12 as by plastic welding or bonding. Rotation of the knob 30 is indexed by circumferentially spaced detents 46 in the knob 30 which accept complementary projections 43 on the hub 20. As seen in FIG. 3, the attachment points 47 of the cords 40 and 42 to the insertion end 16 of the tube 12 are on the interior of the tube 12. The cords 40 and 42 are routed internally of the catheter 12 in freely slidable relation thereto, thence outwardly of the catheter 12 and through a pair of apertures 48 and 50 in the flange 28 of the hub 20.

When the control knob 30 is rotated, the retraction cords 40 and 42 are wound around the inner cylinder 22 of the hub 20 which functions as a spool. The cords 40 and 42 draw the insertion end 16 of the tube 12 toward the hub 20 shortening and thereby mechanically radially expanding the tube 12.

In operation, the intravenous catheter 10 is telescoped over the needle 25 prior to insertion thereof into a blood vessel 60. After the needle 25 punctures the blood vessel 60, the insertion end 16 of the catheter 12 is advanced thereinto. Thereafter, the needle 25 may be removed and a larger diameter tube 62 inserted into the catheter 10.

As seen in FIG. 7, rotation of the catheter control knob 30 effects winding of the cords 40 and 42 about the inner cylinder 22 of the hub 20, thereby axially shortening and radially expanding the catheter 12 to the full inside diameter of the blood vessel 60.

To effect removal of the intravenous catheter 10, the cap 30 is rotated in a direction opposite to the direction of initial rotation thereby relaxing tension on the cords 40 and 42 and allowing the tube 12 to return, by memory, to its inherent minimum diameter configuration.

The intravenous catheter 10 can then be removed from the blood vessel 60 without damage thereto.

While the preferred embodiment of the invention has been disclosed, it should be appreciated that the invention is susceptible of modification without departing from the scope of the following claims.

I claim:

1. An expandable intravenous catheter for the rapid infusion of fluids into a blood vessel comprising:

a radially expandable fluid impervious tube comprising a membrane having oppositely helically wound fibers therein, said fibers being wound to a predetermined minimum diameter and having a memory so as to constantly bias said membrane to said minimum diameter, the diameter of said tube being expandable against the bias exerted by the memory of said fibers upon axial movement of the ends of the tube toward one another;

a hub on one end of said tube;

a rotatable spool journaled on said hub; and a plurality of cords connected, respectively, to an opposite end of said tube and to the spool on said hub, rotation of said spool effecting tensioning of said cords and movement of the opposite end of said tube toward said hub thereby to expand said catheter in direct infinitely controllable relation to the angle of rotation of said spool.

* * * * *